United States Patent [19]

Reiner

[11] 4,393,067
[45] Jul. 12, 1983

[54] NICOTINOYL ESTERS FOR ANALGESIC AND ANTI-INFLAMMATORY TREATMENT

[75] Inventor: Alberto Reiner, Como, Italy

[73] Assignee: D and D Srl, Milan, Italy

[21] Appl. No.: 325,029

[22] Filed: Nov. 25, 1981

Related U.S. Application Data

[63] Continuation-in-part of Ser. No. 225,978, Jan. 19, 1981, abandoned.

[30] Foreign Application Priority Data

Jan. 19, 1980 [IT] Italy .................. 19354 A/80

[51] Int. Cl.³ .................. A61K 31/435; C07D 213/62
[52] U.S. Cl. .................. 424/256; 546/270; 546/261; 546/263
[58] Field of Search .................. 546/270, 261, 263; 424/256

[56] References Cited

U.S. PATENT DOCUMENTS 3,557,131  1/1971  Yoshimura et al. .................. 424/256

Primary Examiner—John M. Ford
Assistant Examiner—Robert C. Whittenbaugh
Attorney, Agent, or Firm—Murray and Whisenhunt

[57] ABSTRACT

The nicotinic ester of (3-4)-O-isopropylidene pyridixole having the formula:

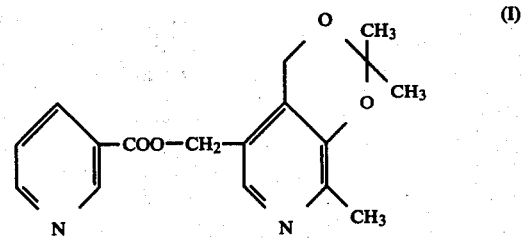

shows analgesic and anti-inflammatory activity.

6 Claims, No Drawings

NICOTINOYL ESTERS FOR ANALGESIC AND ANTI-INFLAMMATORY TREATMENT

CROSS-REFERENCE TO RELATED APPLICATION

This application is a continuation-in-part of my earlier application Ser. No. 225,978, filed Jan. 19, 1981, now abandoned.

The present invention relates to nicotinoyl ester of (3-4)-O-isopropylidene pyridoxine and the hydrochloride thereof having the formula:

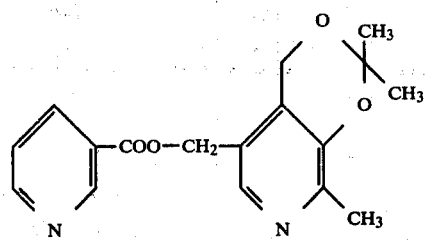

which is endowed with interesting pharmacological properties by which it is useful for particular therapeutical uses. The compound of the invention is in the form of a white microcrystalline powder, partially soluble in water and substantially isoluble in organic solvents.

The U.S. Pat. No. 3,557,131 and the U.K. Pat. No. 1,070,120 disclose the chemical compound of the invention, as well as the corresponding 5-O-nicotinyl-pyridoxine, their preparation and the possible use as anti-atherosclerosis, hypocholesterolemic any hypoglycemic drugs.

It has now been found, surprisingly, that the compound of the invention shows an unexpected and totally different therapeutical effect, it being useful as an analgesic and anti-inflammatory drug, practically devoid of gastric lesivity. For the preparation of the compound of the invention, hydrochloride chloride of the nicotinic acid is reacted with triethylamine and (3-4)-O-isopropylidene pyridoxine at the temperature of 50°-55° C. under stirring, giving place to the reaction product as a base which is converted to the hydrochloride (nicotinic ester).

The following example describes, in an illustrative but non limiting sense, the preparation of the compound of the invention.

EXAMPLE

Nicotinic ester of (3-4)-O-isopropylidene pyridoxine

In a four neck flask, having a stirrer, cooling means, thermometer and dropping funnel, 24 g of hydrochloride chloride of nicotinc acid and 200 mls of carbonium tetrachloride are charged, the flask being simultaneously cooled by an ice-water bath to maintain the temperature at a value not higher than 10° C., preferably 5° C.

Then 16.5 g of triethylamine are added, the cooling being continued, and thereafter the simultaneous addition of further 16.5 g of triethylamine, and of 31.5 g (of (3-4)-O-isopropylidene pyridoxine takes place.

At the end of the addition the temperature of the flask is brought to 50°-55° C. and maintained thereto for about 2 hours under stirring, the reaction mass being then slowly cooled during about 12 hours.

After a filtration for the separation of the triethylamine hydrochloride, the reaction mixture is concentrated under vacuum and the residual oil is taken with about 250 mls of methylisobutylketone.

The desired product (32 g.) namely nicotinic ester of (3-4)-O-isopropylidene pyridixol, crystallizes and is converted to the hydrochloride by treatment with gaseous hydrogen chloride in the stechiometrical ratio.

The product, having molecular weight 350.812 and melting point of 153°-157° C. (with dec.) is fairly soluble in alcohol, poorly soluble in water (it is hydrolized at pH 4) and insoluble in toluene and $CHCl_3$.

The analysis for $C_{17}H_{19}N_2O_4Cl$ gives: calc. (%): C, 58.20; H, 5.45; N, 7.98; Cl, 10.10. found (%): C, 58.00; H, 5.10; N, 7.85; Cl, 9.95.

The compound of the invention has been tested as regards both toxicity and pharmacological effects, with the following results:

(A) Acute toxicity

The tests have been carried out in the rat, by administering per os doses of 1000 and 2000 mg/kg of the test compound and doses from 863.15 to 1921.73 mg/kg of acetylsalicylic acid.

Whereas for the test compound no death was detected, whereby the $LD_{50}$ value could not be calculated, for the comparison compound an $LD_{50}$ value of 1450 mg/kg was found.

By endoperitoneal route the test compound was administered at doses of 500 to 1333.33 mg/kg and the comparison compound at doses of 256 to 500 mg/kg.

The following data were obtained:
Test compound: $LD_{50}$=910(758.33–1092.0) mg/kg
acetylsalicycli acid: $LD_{50}$=350(277.78–441.0) lg/kg In the mouse for the test compound, the $LD_{50}$ is 2000 (1801.8–2220.0) mg/kg/os, whereas for the acetylsalicylic acid and $LD_{50}$ is 1200 (1052.63–1368.0) mg/kg/os.

(B) Gastric tolerability

The comparison compound, acetylsalycilic acid, has been administered at doses from 31.25 to 125 mg/kg/os to rats fasted since 18 hours, and at doses of 15.62 to 62.5 mg/kg to rats fasted since 48 hours. The $UD_{50}$ values were respectively:
$UD_{50}^{18h}$=62.5 mg/kg/os
$UD_{50}^{48h}$=28 mg/kg/os For the compound of the invention, tested at doses of 62.5 to 1000 mg/kg/os both in rats fasted since 18 hours and in rats fasted since 48 hours, no signs of gastric lesions are found even at doses of 500 and 1000 mg/kg.

(C) Anti-inflammatory activity

The anti-inflammatory activity has been assessed according to the test of the oedema induced by carrageenin. The doses of the test compound and the acetylsalicylic acid were from 40 to 320 mg/kg/ per os, and the following values of $ED_{50}$ were found:
after 3 hours:
test compound: $ED_{50}$=133.2 mg/kg/os
acetylsalicylic acid: $ED_{50}$=120.87 mg/kg/os
after 6 hours:
test compound: $ED_{50}$=373.33 mg/kg/os
acetylsalicylic acid: $ED_{50}$=189.21 mg/kg/os

(D) Analgesic activity (Randall-Selitto test)

The analgesic effect on the pain of the inflammed paw was tested with doses of 20 to 320 mg/kg/os.

The following values of $ED_{50}$ were found:

| | | after 3 hours | after 6 hours |
|---|---|---|---|
| test compound | $ED_{50}$ | 31.07 mg/kg | 59.94 mg/kg |
| acetylsalicylic acid | $ED_{50}$ | 38.46 mg/kg | 81.67 mg/kg |

| Compound | $LD_{50}$ per os in the rat mg/kg | $UD_{50}$ per os in the fasted rat after 18 h | $UD_{50}$ per os in the fasted rat after 48 h | Carrageenin induced oedema $ED_{50}$ (3 h) mg/kg | $ED_{50}$ Randall-Selitto (3 h) mg/kg |
|---|---|---|---|---|---|
| Indomethacin | 21 | 6.90 | 3.45 | 4.40 | 1.33 |
| Diflunisal | 580 | N.C. (400) | N.C. (400) | 23.29 | 8.78 |
| Ketoprofen | 45 | 2.52 | 0.92 | 0.43 | 0.20 |
| Ibuprofen | 620 | 26.50 | 8.00 | 48.00 | 1.32 |
| Aspirin | 1450 | 62.50 | 28.00 | 120.87 | 38.46 |
| Compound of the invention | >2000 | N.C. (1000) | N.C. (1000) | 133.30 | 31.07 |

N.C. = Not Calculable (in brackets the maximum administered dose)
Indomethacin: 1-(p-chlorobenzoyl)-5-methoxy-2-methyl-indol-3-acetic acid
Diflunisal: 5-(2,4-difluorophenyl)-2-hydroxy-benzoic acid
Ketoprofen: 2-(3-benzoylphenyl)-propionic acid
Ibuprofen: 2-(4-isobutylphenyl)-propionic acid
Aspirin: acetylsalicylic acid Lastly in the following table the corresponding values of the main parameters ($LD_{50}$, $D_{50}$ and $ED_{50}$) of the main drugs having anti-inflammatory activity are reported.

From the table it will be seen that the compound of the invention is particularly advantageous especially for the gastric tolerability, the analgesic and antiflammatory effect being either the same or higher, over the known drugs which however have no chemical relationship with the compound of the invention.

The compound of the invention can be used for the preparation of pharmaceutical compositions, useful for oral and rectal administration, together with the well known excipients, vehicles and fillers, and prepared according to the known art.

For the oral administration tablets, capsules and pills are foreseen, containing 200 to 700 mg of active compound.

As regards the treatment of acute states of inflamation and pain the admistraton of 600 to 1800 mg per day is considered.

I claim:

1. A method for the treatment of inflammation in a patient in need of such treatment, said method comprising administering to said patient a therapeutically effective amount of the nicotinoyl ester of (3-4)-O-isoproylidene pyridoxine.

2. A method for inducing analgesia in a patient in need of such analgesia, said method comprising administering to said patient a therapeutically effective amount of the nicotinoyl ester of (3-4)-O-isopropylidene pyridoxine.

3. A method according to claim 1, wherein said ester is administered at a daily dosage level of 600 to 1800 mg.

4. A method according to claim 2 wherein said ester is administered at a daily dosage level of 600 to 1800 mg.

5. A method according to claim 1 wherein said ester is administered orally or rectally.

6. A method according to claim 2 wherein said ester is administered orally or rectally.

* * * * *